(12) United States Patent
Park

(10) Patent No.: US 7,213,536 B2
(45) Date of Patent: May 8, 2007

(54) METHOD FOR PRODUCING SHORT-LIVED SALT-TOLERANT FRESHWATER BAITFISH

(75) Inventor: Eric Douglas Park, Lonoke, AR (US)

(73) Assignee: I.F. Anderson Farms, Inc., Lonoke, AK (US)

( * ) Notice: Subject to any disclaimer, the term of this patent is extended or adjusted under 35 U.S.C. 154(b) by 36 days.

(21) Appl. No.: 10/970,945

(22) Filed: Oct. 22, 2004

(65) Prior Publication Data

US 2006/0086323 A1    Apr. 27, 2006

(51) Int. Cl.
*A01K 61/00* (2006.01)

(52) U.S. Cl. ..................... 119/217; 119/215

(58) Field of Classification Search ........... 119/215, 119/231, 217, 268, 245, 228, 220, 216; 800/20
See application file for complete search history.

(56) References Cited

U.S. PATENT DOCUMENTS

| | | | |
|---|---|---|---|
| 2,699,751 A | | 1/1955 | Hasler et al. |
| 3,406,662 A | * | 10/1968 | Karstein et al. ............ 119/217 |
| 3,777,709 A | * | 12/1973 | Anderson et al. ........... 119/217 |
| 4,363,290 A | * | 12/1982 | Kunz et al. ................ 119/231 |
| 4,509,458 A | * | 4/1985 | Rines et al. ............... 119/217 |
| 5,048,458 A | | 9/1991 | Ebner et al. |
| 5,485,808 A | * | 1/1996 | Huebner .................... 119/231 |
| 6,016,770 A | * | 1/2000 | Fisher ...................... 119/215 |
| 6,463,883 B1 | * | 10/2002 | Harris et al. ............... 119/230 |
| 6,932,025 B2 | * | 8/2005 | Massingill et al. .......... 119/216 |
| 2003/0166908 A1 | | 9/2003 | Harris et al. |

OTHER PUBLICATIONS

OSU Department of Fisheries and Wildlife, "Saprolegnia: There's a fungus among us", Jul. 2003, pp. 1-8 (Saprolegnia), http://web.archive.org/web/20030710220412/http://hmsc.oregonstate.edu/classes/MB492/saprokent/saprolegnia.htm.*

* cited by examiner

*Primary Examiner*—Teri Pham Luu
*Assistant Examiner*—Joshua Michener
(74) *Attorney, Agent, or Firm*—Mark Murphey Henry; Nathan Price Chaney

(57) ABSTRACT

A method for selecting a freshwater fish able to tolerate conditions of varying salinity is disclosed. Fish are first selected by pre-screening for salt-tolerance. The selected fish are bred using techniques essentially described herein. The offspring of the selected fish may then be subjected to additional factors to increase salt-tolerance. Thereafter, the offspring are reared in normal freshwater conditions resulting in a freshwater fish suitable for brief exposures to saltwater conditions.

11 Claims, No Drawings

METHOD FOR PRODUCING SHORT-LIVED SALT-TOLERANT FRESHWATER BAITFISH

CROSS REFERENCES

None.

GOVERNMENT RIGHTS

None.

BACKGROUND OF THE INVENTION

Currently, saltwater baitfishes are the preferred live bait of saltwater anglers. The majority of saltwater anglers gather live bait or use artificial bait sources, causing the numbers of natural saltwater baitfish to be lower than ever. In recent years, the Gulf of Mexico states have reported that during winter months the supply of live bait is not sufficient to meet the demand of saltwater anglers. On May 15, 2003, the journal Nature reported that oceanic fish species worldwide have been so systematically over-harvested that fewer than ten percent of 1950 levels remained. Further, collecting live saltwater bait is often subject to local bag limits because the harvest and use of a native species as bait increases pressure on the saltwater ecosystem as a whole.

Several additional factors that discourage anglers from using live bait include the following: the lack of immediate availability, the increased time associated with collecting live bait from the wild, and the sensitivity of natural baitfish to artificial living environments needed to store the baitfish until used. The inventor views the limited availability of saltwater baitfish as a severe problem, both for the native saltwater fish population as well as the sport-fishing industry.

A clear need exists for short-lived salt-tolerant freshwater baitfish that are tolerant to limited exposure to saltwater conditions associated with saltwater angling. Such baitfish must operate as living, moving, highly desirable bait for a limited time, yet must have only limited saltwater tolerance such that extended exposure will eventually kill the fish. Aquaculture production of short-lived salt-tolerant freshwater baitfish will provide alternative sources of stocks, will decrease demand on natural populations of native fishes, and will help satisfy the growing demand of saltwater angling. Moreover, the use of short-lived salt-tolerant freshwater baitfish will accomplish these tasks without jeopardizing the health of native fishes, without decreasing natural food supplies, and without introducing normative fish to saltwater ecosystems. As such, the present invention links the spheres of artificial bait and the use of native saltwater species as baitfish.

Three major species are cultured for freshwater bait—the golden shiner, *Notemigonus crysoleucas*; the goldfish, *Carassius auratus*; and the fathead minnow, *Pimephales promelas*. These three species are easily spawned and are popular as freshwater aquaculture fishes because they are easy to raise and harvest. As a result, these fishes have been used in freshwater aquaculture systems for many years. However, these fishes have a terribly short lifespan when exposed to saltwater conditions, lasting less than a few minutes.

A simple method for producing short-lived salt-tolerant freshwater baitfish not based upon an artificial modification of the genome of the fish is highly desirable. The present invention contemplates the use of highly selective breeding techniques and the use of specialized breeding stations to identify normative genetic pressure changes and to select only those short-lived salt-tolerant freshwater baitfish that are capable of sustaining life in saltwater conditions for a duration sufficient to meet the needs of the saltwater sport fishing industry.

BRIEF SUMMARY OF THE INVENTION

The present invention relates to a method of screening freshwater fish, fish eggs, and fish fry that accelerates the induction of useful and desirable traits in freshwater fish that are not otherwise found in nature or can only be induced by committing substantial additional investment in time and material resources. The overall objective of this invention produces an economically viable production system capable of providing a year-round supply of short-lived salt-tolerant freshwater baitfish for use as live bait in the saltwater sport fishing industry.

It is a goal of the present invention to provide a method for selecting short-lived salt-tolerant freshwater baitfish in which the fish's natural physiology is maintained.

It is another goal of the present invention to provide a method for reliably selecting a short-lived salt-tolerant freshwater baitfish for breeding based on its level of salt-tolerance.

It is yet another goal of the present invention to provide a method for reliably selecting short-lived salt-tolerant freshwater baitfish in which fish are temporarily exposed to an artificial saline environment yet are reintroduced to fresh water following a specialized selection regimen.

It is yet another goal of the present invention to provide a method for applying non-native genetic mutation pressure to fish.

It is yet another goal of the present invention to provide a method for applying non-native genetic mutation pressure to fish fry.

It is yet another goal of the present invention to provide a method for pre-screening fish for short-lived high salt-tolerance.

It is yet another goal of the present invention to provide a method for selecting short-lived salt-tolerant freshwater baitfish by exposing freshwater fish eggs to a saline environment for a predetermined amount of time before the freshwater fish eggs are reintroduced to fresh water to continue forward with natural development.

It is yet another goal of the present invention to provide a method for selecting short-lived salt-tolerant freshwater baitfish by exposing freshwater fish fry to a saline solution for a predetermined amount of time, and reintroducing the freshwater fish fry to fresh water to continue forward with natural development.

Thus, the goal of the present invention is to provide a method for producing a short-lived salt-tolerant freshwater baitfish capable of sustaining life in saltwater conditions sufficient to meet the needs of the saltwater sport fishing industry. This method comprises selecting freshwater fish by pre-screening for salt-tolerance, breeding freshwater fish with salt-tolerance in mind, and subjecting their offspring to additional screening for salt-tolerance. The methodological process comprises selecting freshwater fish and freshwater fish offspring with a short-lived salt-tolerance and rearing the freshwater fish in normal conditions until the freshwater fish are needed as live baitfish.

DETAILED DESCRIPTION OF THE PREFERRED EMBODIMENT

What is disclosed is a method for selecting a freshwater fish of short-lived salt-tolerance comprising the steps of screening fish for salt-tolerance, selecting and breeding fish offspring that are predisposed to a short-lived salt-tolerance, and screening the fish offspring for an established salt-tolerance. The fish produced thereby are reared in normal freshwater conditions. While any number of these steps can accomplish the goals, or a part of them, this disclosure sets forth a comprehensive approach. This is not intended to limit to only the combination of all these steps unless claims proscribe otherwise.

In the first screening step, a shop-lived salt-tolerant freshwater baitfish is selected by subjecting freshwater fish to an artificial, increased saline environment. The heightened saline environment is preferably prepared by the addition of amounts of chlorine, s odium, sulfur, magnesium, calcium, and/or potassium salt to fresh water because these elements make up about 99% of the salts in seawater, although other substances may be added to the water to create an artificial environment that can be used to produce salt-tolerance in fish. The concentration and amounts of salt added to the water may vary as needed to accomplish the present invention. One solution of the present invention is to add sodium chloride to fresh water; in particular, sea salt is added to fresh water to bring the salinity to about 32 parts per thousand ("PPT"), although ranges upwards of 500 PPT may be used.

The purpose of the first screening step is to select for fish that are able to withstand high salt concentrations for a given period; that is, the selection produces fish predisposed to a short-lived salt-tolerance. This first screening step may be repeated on the same fish or offspring thereof to produce a fish of desired salt-tolerance, or to fit within a range of saline conditions.

The first screening step of the present invention is preferably done in the autumn of the year prior to the desired spring spawn. The saline solution is prepared in a tank commonly referred to in the industry as a raceway, although the invention is not limited thereto. The tank has an inflow and a discharge end. The fish are preferably placed in the tank near the discharge end and are kept in this area using a divider. Upon exposing the fish to the saline environment for a predetermined length of time, the divider is removed and a steady flow of fresh water is established in the tank. Those fish not sufficiently adaptable to the saline environment are expelled with the outflow of fresh water while the salt-tolerant individuals are able to recover strength and instinctively swim upstream. The upstream survivors are returned to a freshwater source for use the as broodstock.

In the second screening step, the broodstock used for production of salt-tolerant eggs are preferably selected from the screening step disclosed above. In the egg-screening process, the eggs are subjected to an artificial, increased saline environment described above for a predetermined amount of time. Following this exposure to the saline environment, the eggs that survive are reintroduced to fresh water and allowed to mature.

In the third salt-tolerance screening process, fry are subjected to an alternating regimen of saline environment and fresh water. These fry are the product of the salt-tolerant eggs, now matured, disclosed above. This process is performed to produce and select for fish that have an increased ability to withstand alternating exposure to a saline environment when compared to freshwater fish that were not subjected to any of the screening steps.

While it is preferred to produce a short-lived salt-tolerant freshwater baitfish by performing each of the above steps in succession, the advantages of the invention may be achieved by performing any of the steps alone or in varying combinations. Producing a short-lived salt-tolerant freshwater baitfish through performing all of the above steps on an individual is especially preferred since it produces a greater consistency and populous of desired short-lived salt-tolerant freshwater baitfish. By using multiple screening techniques to achieve consistency, the genetically pressured elements become more stable and predictable.

Bearing the screening steps above in mind, the preferred embodiment of the invention can now be disclosed. The preferred embodiment begins with selection of broodstock by adding sea salt to fresh water to form a saline solution that has a salt content of about 32 PPT. A tank having both an inflow and discharge mechanism fills with this solution. A divider placed in the tank keeps fish located near the discharge end. Fish placed into the tank between the divider and the discharge end remain exposed to the saline solution for about forty-five minutes. At the end of this period, introduction of fresh water forms a substantial current in the tank. Removal of the divider allows salt-tolerant fish to swim upstream in the tank towards the inflow end, while fish lacking salt-tolerance flush out the discharge mechanism. Those fish that are capable of swimming upstream qualify as broodstock, and the criteria, such as salt content and time left in high salinity, may vary.

The brooders selected then spawn in a controlled freshwater environment. An acclimation tank fills with water replicating spawning conditions. The brooders adjust to this environment for twenty-four hours, at which time the water temperature should be around 72° F. The brooders move to a spawning tank through an automatic transfer pipe to reducing harmful handling. The spawning tank is a two-level tank with a deep center shelf and shallow shelves that are wider than the deep shelf. When the brooders arrive via the transfer pipe in the spawning tank, the water level is low enough that the shallow shelves are above the waterline. The shallow shelves are populated with artificial spawning material, and over a ten-hour period during the evening the water level rises until the spawning material becomes covered by the proper amount of water for the species of fish in question. The water level is reduced the following morning to a depth where the shallow shelves are again above the waterline and the fish occupy the deep shelf. The brooders are transferred to another tank once spawning is complete. A hatchery receives the artificial spawning materials that now contain fertilized fish eggs.

The hatchery is responsible for incubation, hatching, and limited maturation of the eggs deposited on the spawning materials. The spawning materials are preferably flat, rectangular pieces of material known as mats. These mats stack and maintain spacing between them in a hatching tank to allow for circulation. Water temperature in the hatching tank is held steady at 70° F. As a next step, sea salt is added to bring the salinity of the tank to 32 PPT. The lowered addition of sea salt holds the salinity at 32 PPT for a sufficient duration, at which time the normal water exchange dilutes the salt content to a freshwater level. Twenty-four hours after fry hatch, the addition of sea salt brings the salinity of the tank to 10 PPT. After a sufficient period, the normal water exchange again dilutes the salt content of the water in the hatching tank. Twenty-four hours following exposure to the salt treatment, the fry are transferred into growing ponds for maturation.

The fry that mature compose the short-lived salt-tolerant freshwater baitfish of the present invention. Some of the stock of baitfish produced by the disclosed method are retained for use a brooders in another cycle of baitfish production. Using broodstock selected from the entire disclosed preferred embodiment produces additional, longer lasting salt-tolerance in successive generations of baitfish.

What is claimed is:

1. A method for selecting short-lived salt-tolerant freshwater baitfish, comprising:
    (a) introducing one or more freshwater fish to a saline solution;
    (b) subjecting the one or more freshwater fish to a steady flow of fresh water while said one or more freshwater fish are still in said saline solution;
    (c) selecting brooders from the one or more freshwater fish that swim upstream into the flow of freshwater and
    (d) transferring and reintroducing the brooders to freshwater.

2. The method of claim 1 wherein the saline solution has a concentration greater than 10 parts per thousand (PPT) up to 500 PPT.

3. The method of claim 1 wherein the saline solution is comprised of sea salt added to fresh water.

4. The method of claim 1 wherein the introduction at step (a) further comprises use of a tank, the tank comprising an inflow port and an effluent port; and the freshwater fish are introduced into the saline solution near the effluent port of the tank.

5. The method of claim 1 wherein the introduction at step (a) further comprises use of a tank, the tank comprising an inflow port, an effluent port, and a divider, the divider being placed between the inflow port and the effluent port of the tank; the freshwater fish being placed into the saline solution near the effluent port; and, after a predetermined period, the effluent port opened, the divider removed, and the freshwater fish subjected to the flow of fresh water from the inflow port.

6. A method for selecting short-lived salt-tolerant freshwater baitfish fry, comprising:
    (a) exposing freshwater fish fry to a saline solution having a concentration greater than 10 PPT up to 500 PPT;
    (b) subjecting the freshwater fish fry to a steady flow of fresh water while the freshwater fish fry are still in said saline solution;
    (c) selecting freshwater fish fry from those swimming upstream into the flow of freshwater and
    (d) transferring and reintroducing the selected freshwater fish fry to fresh water for growth to maturity.

7. A method for selecting short-lived salt-tolerant freshwater baitfish, comprising:
    (a) selecting freshwater fish brooders by screening for short-lived salt-tolerance;
    (b) exposing offspring of the freshwater fish brooders to a saline solution;
    (c) selecting the offspring that demonstrate salt-tolerance; and
    (d) reintroducing the selected offspring to fresh water.

8. The method of claim 7 wherein the saline solution at step (b) has a salinity greater than 10 PPT up to 500 PPT.

9. The method of claim 7 wherein the fresh water at step (d) is treated to reduce fungal infection in the offspring.

10. A method for producing a short-lived salt-tolerant freshwater baitfish, comprising:
    (a) preparing a saline solution having a salinity of about 32 PPT in a tank, the tank comprising an inflow port and an effluent port;
    (b) placing a divider into the tank;
    (c) introducing freshwater fish to the saline solution between the divider and the effluent port of the tank;
    (d) allowing the freshwater fish to remain in the saline solution for about 45 minutes;
    (e) subjecting the freshwater fish to a stream of fresh water while simultaneously opening the effluent port of the tank and removing the divider, the stream of fresh water entering through the inflow port of the tank and exiting through the effluent port of the tank;
    (f) selecting brooders from the freshwater fish which are able to swim upstream within about 5 minutes of initiating the flow of the stream of fresh water;
    (g) acclimating the brooders to spawning water conditions over a period of about 24 hours, the spawning water conditions having a final temperature of about 72° F.;
    (h) transferring the brooders to a spawning tank, the spawning tank comprising one or more deep shelves and one or more shallow shelves;
    (i) maintaining a water level of the spawning water so the brooders can only occupy the deep shelf of the tank;
    (j) placing spawning material on the shallow shelf of the spawning tank;
    (k) adjusting water flow so that over a period of about 10 hours the spawning water floods the shallow shelf of the spawning tank until the water depth of the spawning water over the spawning material has reached the predetermined depth corresponding to the species of the brooders;
    (l) allowing the brooders to spawn;
    (m) collecting eggs of the brooders on the spawning material;
    (n) reducing the water depth to the point where the shallow shelf is exposed;
    (o) removing the spawning material with the eggs attached thereto;
    (p) placing the spawning material with the eggs attached in a hatchery;
    (q) maintaining the water temperature of the hatchery at about 70° F.;
    (r) exposing the eggs to a saline solution having a salinity of about 32 PPT, for a sufficient period;
    (s) selecting eggs from the hatchery that demonstrate salt-tolerance;
    (t) incubating the eggs in fresh water;
    (u) treating the fresh water to reduce fungal infection in the eggs;
    (v) allowing the eggs to mature and hatch into freshwater fish fry;
    (w) exposing the freshwater fish fry to a saline solution for a effective amount of time, the saline solution having a salinity greater than 10 PPT up to 500 PPT;
    (x) selecting the freshwater fish fry that demonstrate salt-tolerance;
    (y) reintroducing the selected freshwater fish fry to fresh water for growth to desired maturity.

11. The method of claim 1 wherein the saline solution has a concentration greater than 30 PPT up to 500 PPT.

* * * * *